United States Patent
He et al.

(10) Patent No.: US 11,161,860 B2
(45) Date of Patent: Nov. 2, 2021

(54) COMPOUND HAVING EFFECTS OF INHIBITING PHOSPHODIESTERASE 4, PREPARATION METHOD THEREOF AND PHARMACEUTICAL USE THEREOF

(71) Applicants: Hefei Industrial Pharmaceutical Institute Co., Ltd., Anhui (CN); Hefei Amvite Pharmaceutical Co., Ltd, Anhui (CN)

(72) Inventors: Guangwei He, Anhui (CN); Zhaoxing Chu, Anhui (CN); Qinlong Xu, Anhui (CN); Feng Li, Anhui (CN); Weizhong Liu, Anhui (CN); Jiajia Mo, Anhui (CN); Yan Zhao, Anhui (CN)

(73) Assignees: HEFEI INDUSTRIAL PHARMACEUTICAL INSTITUTE CO., LTD, Anhui (CN); HEFEI AMVITE PHARMACEUTICAL CO., LTD., Anhui (CN)

(*) Notice: Subject to any disclaimer, the term of this patent is extended or adjusted under 35 U.S.C. 154(b) by 0 days.

(21) Appl. No.: 16/761,062

(22) PCT Filed: Dec. 25, 2018

(86) PCT No.: PCT/CN2018/123420
§ 371 (c)(1),
(2) Date: May 1, 2020

(87) PCT Pub. No.: WO2019/134556
PCT Pub. Date: Jul. 11, 2019

(65) Prior Publication Data
US 2021/0179640 A1    Jun. 17, 2021

(30) Foreign Application Priority Data
Jan. 4, 2018    (CN) .......................... 201810007608.5

(51) Int. Cl.
*C07F 5/02* (2006.01)

(52) U.S. Cl.
CPC .................................. *C07F 5/027* (2013.01)

(58) Field of Classification Search
None
See application file for complete search history.

(56) References Cited

FOREIGN PATENT DOCUMENTS

CN    108148085    6/2018

OTHER PUBLICATIONS

Written Opinion and International Search Report of PCT/CN2018/123420 dated Mar. 26, 2019, 10 pages (English and Chinese).

*Primary Examiner* — Joseph R Kosack
(74) *Attorney, Agent, or Firm* — Rankin, Hill & Clark LLP

(57) ABSTRACT

The disclosure relates to the field of medicinal chemistry, in particular, to a class of small molecule compounds for inhibiting phosphodiesterase 4 (I), a preparation method thereof and a pharmaceutical composition comprising the compound. The pharmacodynamic test proves that the compound of the disclosure has the inhibitory activity of PDE-4 enzyme and the efficacy of inflammation treatment.

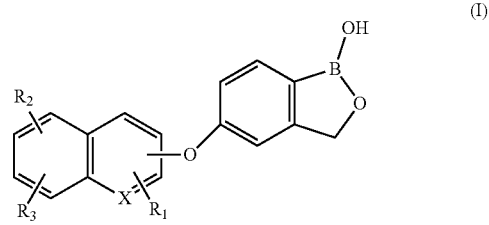

7 Claims, No Drawings

COMPOUND HAVING EFFECTS OF INHIBITING PHOSPHODIESTERASE 4, PREPARATION METHOD THEREOF AND PHARMACEUTICAL USE THEREOF

TECHNICAL FIELD

The disclosure relates to the field of medicinal chemistry, in particular, to a class of small molecule compounds for inhibiting phosphodiesterase 4, a preparation method thereof and a pharmaceutical composition comprising the compound, and a therapeutic use thereof.

BACKGROUND

Inflammation is a common pathological process. Traumatic infections on the body surface and most common and frequently-occurring diseases of various organs (such as furuncle, carbuncle, pneumonia, hepatitis, nephritis, etc.) are inflammatory diseases. [Cruz-Migoni S, Caamaño J. Fat-Associated Lymphoid Clusters in Inflammation and Immunity[J]. Front Immunol. 2016, 7: 612]. Currently, the main clinical methods for treating inflammatory diseases are using topical or systemic hormonal drugs, which have obvious side effects. Searching and discovering a non-hormonal drug with stronger anti-inflammatory activity has been the goal of drug developers.

Phosphodiesterase 4 (PDE4) is a major PDE expressed in neutrophils and T cells, suggesting that a PDE4 inhibitor can effectively control inflammation. Inhibiting PDE4 in inflammatory cells can affect various specific responses, such as the production or release of proinflammatory mediators including cytokines and reactive oxygen species, and has significant effects in the treatment of asthma, COPD, inflammatory bowel disease, atopic dermatitis, psoriasis and rheumatoid arthritis. However, PDE4 isoenzyme inhibitors currently in clinical use, such as rolipram, piclamilast, CDP-840 and avery etc., all have side effects such as vomiting, liver toxicity, and skin irritation, with either failure in drug clinical trials or limitation in the clinical application. It is still necessary to find a new highly effective and low toxicity phosphodiesterase-4 inhibitor for the treatment of inflammatory diseases.

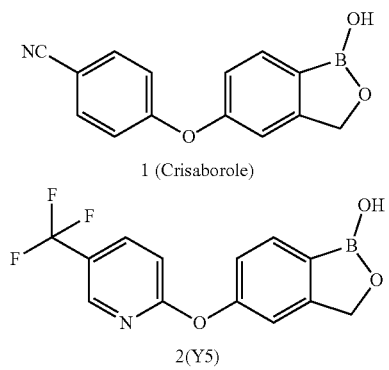

1 (Crisaborole)

2 (Y5)

US20060234981 discloses a class of boron-containing small molecule compound 1 (Crisaborole), which inhibits PDE4 enzyme and has anti-inflammatory activity. I have previously published a compound 2 (Y5) in the patent CN106831840, which showed superior anti-inflammatory activity to Crisaborole. The disclosure designs and synthesizes a series of new compounds, and it is unexpectedly found that these compounds show significantly better effects and utilization than Crisaborole and Y5.

SUMMARY

Based on the previous studies, the disclosure designs and synthesizes a class of compounds having a general formula (I). The pharmacodynamic test proves that the compound of the disclosure may inhibit the activity of the phosphodiesterase 4, and have a use in preventing and treating inflammation-related diseases.

The disclosure is described in detail below.

The disclosure discloses a compound having a general formula (I):

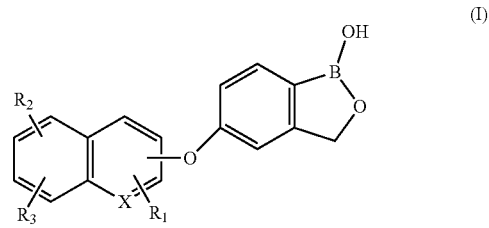

wherein wherein $R_1$, $R_2$, $R_3$ represent an optionally substituted halogen, an alkyl of $C_1$ to $C_6$, a trifluoromethyl, a cyano, an amino, $C(O)OR_a$, $COR_a$, or $OR_a$;

$R_a$ represents H, the alkyl of C1 to C6, the amino or the trifluoromethyl;

X is N or CH.

Preferably, the disclosure includes a compound with the following structures:

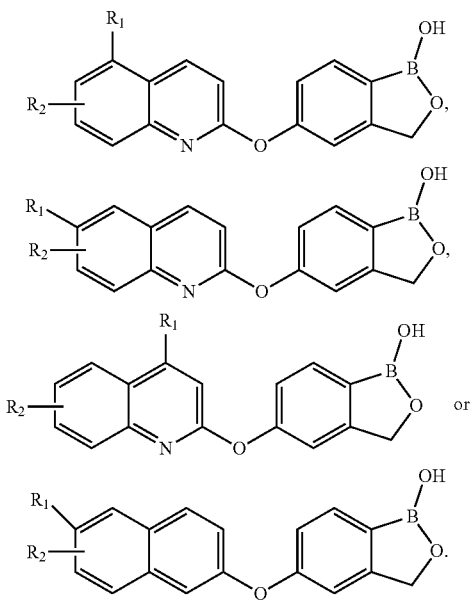

wherein definitions of $R_1$ and $R_2$ are the same as above.

Preferably, the disclosure further includes the following compounds:
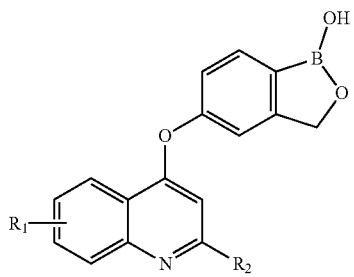
wherein definitions of R₁ and R₂ are the same as above. Some preferred compounds are as follows:
| Compound No. | Structure |
|---|---|
| PD-1 | |
| PD-2 | |
| PD-3 | |
| PD-4 | |
| PD-5 | |
| PD-6 | |
| PD-7 | 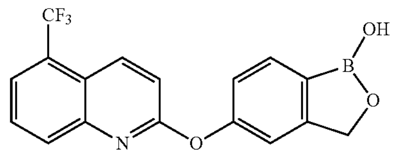 [SMILES: OB1OCc2cc(Oc3ccc4c(C(F)(F)F)cccc4n3)ccc21] |
| PD-8 | 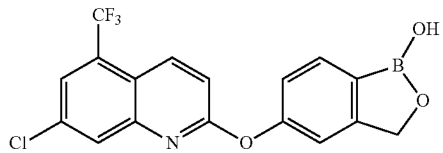 [SMILES: OB1OCc2cc(Oc3ccc4c(C(F)(F)F)cc(Cl)cc4n3)ccc21] |
| PD-9 | 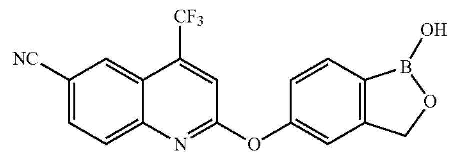 [SMILES: N#Cc1ccc2nc(Oc3ccc4c(c3)COB4O)cc(C(F)(F)F)c2c1] |
| PD-10 | 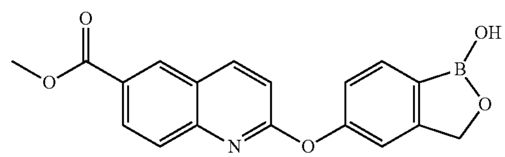 [SMILES: COC(=O)c1ccc2nc(Oc3ccc4c(c3)COB4O)ccc2c1] |
| PD-11 | 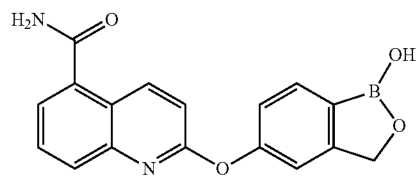 [SMILES: NC(=O)c1cccc2nc(Oc3ccc4c(c3)COB4O)ccc12] |
| PD-12 | 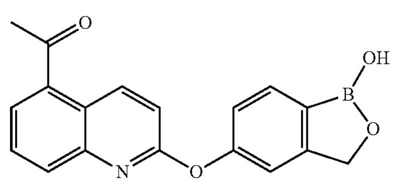 [SMILES: CC(=O)c1cccc2nc(Oc3ccc4c(c3)COB4O)ccc12] |
| PD-13 | 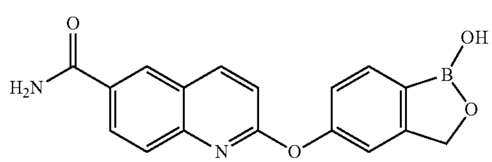 [SMILES: NC(=O)c1ccc2nc(Oc3ccc4c(c3)COB4O)ccc2c1] |
| PD-14 | 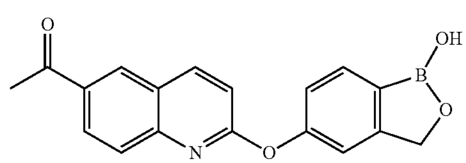 [SMILES: CC(=O)c1ccc2nc(Oc3ccc4c(c3)COB4O)ccc2c1] |
| PD-15 | 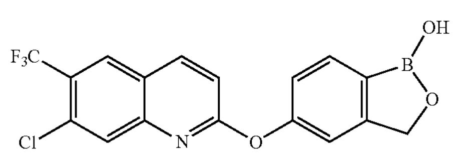 [SMILES: OB1OCc2cc(Oc3ccc4cc(C(F)(F)F)c(Cl)cc4n3)ccc21] |

| Compound No. | Structure |
|---|---|
| PD-16 | 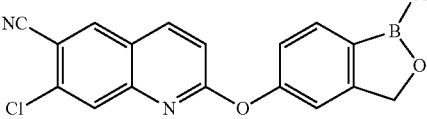 |
| PD-17 | 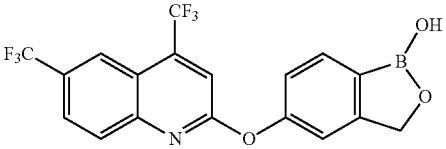 [SMILES: OB1OCc2cc(Oc3cc(C(F)(F)F)c4cc(C(F)(F)F)ccc4n3)ccc21] |
| PD-18 | 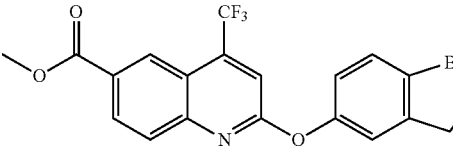 |
| PD-19 | 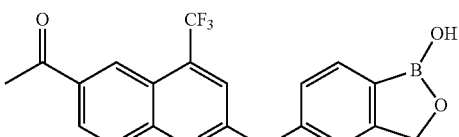 |
| PD-20 | 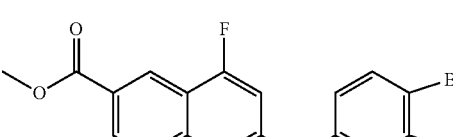 |
| PD-21 | 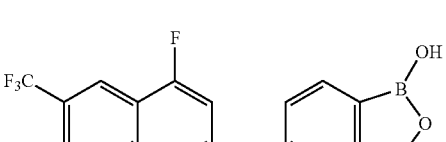 |
| PD-22 | 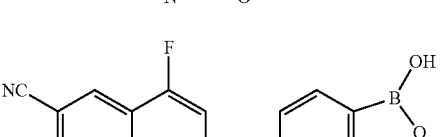 |
| PD-23 | 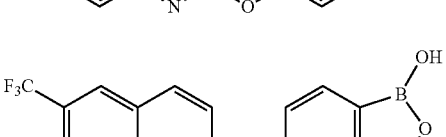 |
| PD-24 | 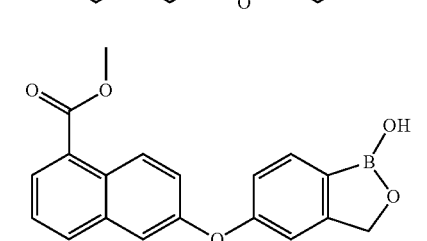 |
| PD-25 | 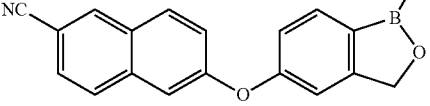 |
| PD-26 | 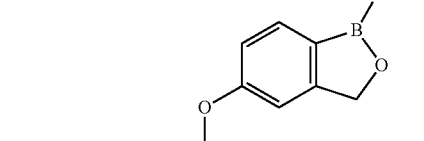 |
| PD-27 | 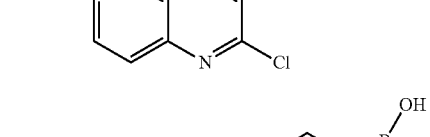 |
| PD-28 | 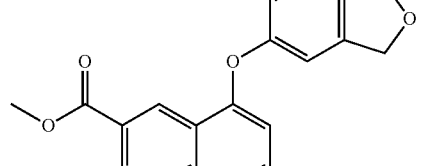 |

The compounds and a pharmaceutically acceptable salt thereof of the disclosure are selected from salts formed from alkali metals or alkaline earth metals, amino acids or basic compounds containing amino groups, or salts formed from pharmaceutically acceptable inorganic or organic acids, preferably are a potassium salt, a sodium salt, an ammonium salt, a hydrochloride, a sulfuric acid, a phosphate salt, a hydrobromic acid, a maleic acid, a fumaric acid, a citric acid, a methanesulfonic acid, a p-toluenesulfonic acid, a tartaric acid or an acetate.

An application of the pharmaceutical composition of the compound or pharmaceutically acceptable salt thereof and the pharmaceutically acceptable carrier according to the disclosure in preparing a drug for treating inflammatory diseases.

In a pharmaceutical composition including the compound according to the disclosure for treating and preventing inflammatory diseases, a therapeutically effective amount of a compound of formula I or a pharmaceutically acceptable salt thereof and a pharmaceutically acceptable carrier are included. The pharmaceutical composition may be in the form of a pharmaceutically conventional preparation such as an ordinary tablet or capsule, a sustained-release tablet or capsule, a controlled release tablet or capsule, a granule, an oral liquid, a syrup, a suppository, a transdermal preparation, an injection, etc.

The preparation method of the compound of the disclosure includes:

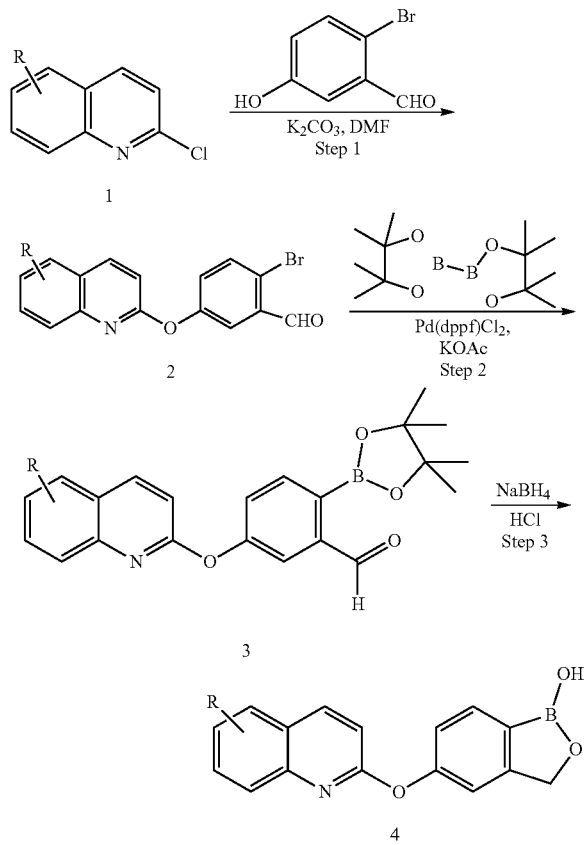

R: cyano, substituted or unsubstituted alkyl, trifluoromethyl, halogen, ester, carboxyl, amido Step 1: condensing a compound 1 and 2-bromo-5 hydroxybenzaldehyde in the presence of protection of a base catalyst such as potassium carbonate, cesium carbonate, sodium carbonate, sodium hydride, potassium tert-butoxide, etc. and nitrogen, with a solvent which may be DMF, DMA etc., and a reaction temperature of 100° C. and 120° C.;
Step 2: dissolving a compound 2 with dioxane, then adding reagents of boronic acid pinacol ester, potassium acetate, palladium, and stirring at 100° C. for 2 hours under nitrogen until the reaction is complete, to obtain a compound 3;
Step 3: dissolving the compound 3 with methanol, slowly adding sodium borohydride, and stirring for 0.5 h at room temperature, then adding 3M hydrochloric acid until a white solid precipitates, to obtain a compound 4.

The preparation of other compounds may refer to the above method.

For biological evaluation, the beneficial effects of the compounds of the disclosure are illustrated by the following experimental data.

The compound of the disclosure has an inhibiting effect on PDE4 enzyme.

The PDE4A enzyme expressed from baculovirus is labeled with N-terminal GST from Sf9 insect cells. A specified PDE4A enzyme and 1 mM cAMP are added to the newly prepared pH 7.5 Tris buffer, the enzyme solution is transferred into reaction wells, and the compound is sonicated in DMSO and then added to the enzyme solution for culturing for 10 minutes at room temperature; the substrate solution is poured into the reaction wells to initiate the reaction and cultured at room temperature for 1 hour, and a detection tracer ($AMP_2/GMP_2$ AlexaFluor 633 Tracer) and an antibody (Transcreener® $AMP_2/GMP_2$ Antibody) are added to stop the reaction for culturing for 90 minutes with gentle mixing. The fluorescence polarization is measured at Ex/Em 620/688, and the test objects are tested at concentrations of 1, 0.1, and 0.01 mM. When the enzyme activity is less than 50%, it is considered to significantly inhibit the activity.

The experimental results are shown in Table 1 below.

TABLE 1

Inhibition of the compound of the disclosure on the activity of PDE4A enzyme

| Compound No. | Enzyme activity | | |
|---|---|---|---|
| | 1 µM | 0.1 µM | 0.01 µM |
| Crisaborole | 11.03 ± 0.52 | 35.17 ± 3.35 | 78.02 ± 05.02 |
| Y5 | 5.56 ± 0.28** | 15.32 ± 1.30** | 61.31 ± 3.18* |
| PD-1 | 3.74 ± 0.71**# | 5.45 ± 1.06**## | 18.79 ± 3.23**## |
| PD-2 | 2.75 ± 0.51**# | 3.80 ± 0.76**## | 7.42 ± 2.11**## |
| PD-3 | 1.98 ± 0.47**# | 4.94 ± 1.56**## | 17.29 ± 1.19**## |
| PD-4 | 1.95 ± 0.18**## | 2.49 ± 0.75**## | 6.17 ± 0.34**## |
| PD-5 | 3.46 ± 1.18**# | 7.27 ± 1.78**# | 9.01 ± 2.02**## |
| PD-6 | 0.32 ± 0.13**# | 0.60 ± 0.10**## | 0.90 ± 0.23**## |
| PD-7 | 1.12 ± 0.99**## | 1.83 ± 0.41**## | 6.41 ± 0.32**## |
| PD-8 | 1.21 ± 0.17**## | 2.25 ± 1.19**## | 4.36 ± 0.59**## |
| PD-9 | 0.99 ± 0.85**## | 1.92 ± 0.39**## | 3.41 ± 0.45**## |
| PD-10 | 1.55 ± 0.67**## | 2.45 ± 0.32**## | 10.79 ± 01.60**## |
| PD-11 | 1.70 ± 0.43**## | 5.85 ± 0.72**## | 10.12 ± 1.93**## |
| PD-12 | 3.46 ± 1.12**# | 6.20 ± 1.23**# | 22.09 ± 0.57**## |
| PD-13 | 1.44 ± 0.40**## | 8.68 ± 0.89**# | 21.73 ± 1.51**## |
| PD-14 | 0.15 ± 0.10**## | 1.26 ± 1.17**## | 3.57 ± 1.08**## |
| PD-15 | 1.08 ± 0.40**## | 0.54 ± 0.50**## | 2.09 ± 0.99**## |
| PD-16 | 0.21 ± 0.57**## | 0.45 ± 0.30**## | 1.05 ± 1.26**## |
| PD-17 | 0.77 ± 0.39**## | 1.89 ± 0.60**## | 4.17 ± 0.99**## |
| PD-18 | 0.13 ± 0.06**## | 0.46 ± 0.35**## | 1.52 ± 0.44**## |
| PD-19 | 0.54 ± 0.47**## | 1.56 ± 0.48**## | 4.22 ± 0.86**## |
| PD-20 | 1.78 ± 0.50**## | 3.64 ± 0.48**## | 6.13 ± 0.93**## |
| PD-21 | 0.28 ± 0.14**## | 0.33 ± 0.23**## | 1.64 ± 0.55**## |
| PD-22 | 1.78 ± 0.63**## | 3.06 ± 0.27**## | 7.16 ± 1.04**## |
| PD-23 | 2.45 ± 0.76**## | 4.51 ± 0.94**## | 9.26 ± 0.73**## |
| PD-24 | 2.64 ± 0.56**# | 7.31 ± 1.16**# | 9.17 ± 1.00**## |
| PD-25 | 2.27 ± 0.74**## | 1.95 ± 1.18**## | 7.17 ± 0.64**## |
| PD-26 | 2.04 ± 0.24**## | 7.23 ± 1.83**# | 12.79 ± 01.82**# |
| PD-27 | 2.69 ± 1.77**# | 9.49 ± 1.59**# | 12.93 ± 01.86**# |
| PD-28 | 2.10 ± 0.93**## | 4.42 ± 0.64**## | 9.14 ± 0.89**## |

(Compared with Crisaborole, *P < 0.05, **P < 0.01; compared with Y5, #P < 0.01, ##P < 0.01)

By testing the inhibition of the compound of the disclosure on the activity of the PDE4 enzyme, it is found that the compounds of the disclosure are superior to Crisaborole and Y5 in inhibiting the activity of the PDE4 enzyme at various concentrations, wherein the compounds PD-4 to PD-9, PD-14 to PD-25, and PD-28 inhibit the PDE4 enzyme by more than 90% at three concentrations.

Compounds of the Disclosure on DNCB-Induced Dermatitis Mouse Model

After female BALB/C mice are selected, each weighing 18-22 g, for animal adaptive breeding for 7 days, these are randomly divided into a blank group, a model group, a positive drug Crisaborole group, a hexadecadrol group, and compound groups, with 8 in each group. Except for the mice in the blank group, the remaining mice are applied with 100 µL of a 1% DNCB solution [acetone: olive oil=4:1 (V/V)] on the skin of the back of the shaved mice, and applied continuously for 3 days once a day. Then, dosing treatment starts 4 days after the mice are housed, and the test drug is applied to the back of each group of animals, wherein animals in the blank group and the model group are applied with a corresponding solvent, the positive drug Crisaborole group and hexadecadrol group are applied with 50 mg/mL of a corresponding drug, and the administration group is applied with 50 mg/mL of a corresponding compound, with 100 μL for each mouse; after application of 4 hours, 0.5% DNCB solution is applied for secondary challenge, and repeated administration and challenge treatment are performed 11 times, once a day. 24 hours after the last administration, the animals are sacrificed, and the back skins (1×0.4 cm$^2$) are taken and fixed in 10% formalin buffer to make pathological sections and perform HE staining; then, the epidermal and dermal layers are observed under a 100× electron microscope, and 5 areas are selected for detection of and recording the skin thickness, and then the average value is taken to represent the final thicknesses of the epidermal layer and dermal layer, respectively.

From the results, it can be known that the compound of the disclosure, hexadecadrol, Crisaborole, and compound Y5 may significantly reduce the thicknesses of the epidermal layer and dermal layer of DNCB-induced atopic dermatitis mice (P<0.01);
specifically, the results are shown in Table 2:

TABLE 2

Effects of the compound of the disclosure on the thickness of skin of DNCB-induced atopic dermatitis mice (Mean ± SD, n = 8)

| Groups | Dose (mg/mL) | Epidermal thickness (μm) | Dermis thickness (μm) |
|---|---|---|---|
| Blank | — | 48.93 ± 07.63 | 194.70 ± 20.55 |
| Model | — | 137.76 ± 10.75$^{ΔΔ}$ | 500.71 ± 28.96$^{ΔΔ}$ |
| hexadecadrol | 50 | 72.14 ± 10.58** $^{a\,a}$ | 377.32 ± 22.05***$^{a\,a}$ |
| Crisaborole | 50 | 105.26 ± 11.35** | 455.14 ± 27.27** |
| Y5 | 50 | 90.14 ± 8.98**$^{\#}$ | 415.08 ± 25.00**$^{\#\#}$ |
| PD-1 | 50 | 75.64 ± 7.86**$^{\#\#}$ $^{a}$ | 385.26 ± 20.17**$^{\#\#}$ $^{a}$ |
| PD-2 | 50 | 100.26 ± 11.35** | 439.76 ± 30.02** |
| PD-3 | 50 | 98.74 ± 9.63** | 420.80 ± 30.55**$^{\#}$ |
| PD-4 | 50 | 70.42 ± 9.24**$^{\#\#}$ $^{aa}$ | 375.06 ± 20.41**$^{\#\#}$ $^{a\,a}$ |
| PD-5 | 50 | 106.74 ± 15.14** | 440.12 ± 23.22** |
| PD-6 | 50 | 70.87 ± 14.43**$^{\#\#}$ $^{aa}$ | 380.15 ± 22.54**$^{\#\#}$ $^{a\,a}$ |
| PD-7 | 50 | 68.21 ± 7.66**$^{\#\#}$ $^{aa}$ | 370.11 ± 24.60**$^{\#\#}$ $^{a\,a}$ |
| PD-8 | 50 | 76.58 ± 8.79**$^{\#\#aa}$ | 385.17 ± 28.85**$^{\#\#}$ $^{a}$ |
| PD-9 | 50 | 97.25 ± 10.43** | 413.25 ± 31.50**$^{\#}$ |
| PD-10 | 50 | 92.17 ± 9.94**$^{\#}$ | 406.74 ± 29.54**$^{\#\#}$ |
| PD-11 | 50 | 95.37 ± 8.75** | 443.17 ± 33.40** |
| PD-12 | 50 | 72.15 ± 8.57**$^{\#}$ $^{aa}$ | 362.44 ± 25.78**$^{\#\#}$ $^{a\,a}$ |
| PD-13 | 50 | 100.23 ± 11.62** | 450.26 ± 25.55** |
| PD-14 | 50 | 75.24 ± 7.98**$^{\#\#}$ $^{aa}$ | 365.40 ± 21.95**$^{\#\#}$ $^{a\,a}$ |
| PD-15 | 50 | 74.28 ± 8.26**$^{\#\#aa}$ | 376.62 ± 23.73**$^{\#\#}$ $^{a\,a}$ |
| PD-16 | 50 | 78.64 ± 9.75**$^{\#\#}$ $^{a}$ | 388.46 ± 24.06**$^{\#\#}$ $^{a}$ |
| PD-17 | 50 | 80.76 ± 10.51**$^{\#\#}$ | 380.74 ± 20.15**$^{\#\#}$ $^{a\,a}$ |
| PD-18 | 50 | 90.35 ± 11.20**$^{\#}$ | 436.16 ± 35.42** |
| PD-19 | 50 | 96.05 ± 9.75** | 441.12 ± 30.17** |
| PD-20 | 50 | 98.74 ± 10.55** | 438.14 ± 29.71** |
| PD-21 | 50 | 70.62 ± 7.12**$^{\#\#}$ $^{aa}$ | 383.34 ± 24.40**$^{\#\#a}$ |
| PD-22 | 50 | 103.45 ± 11.74** | 447.77 ± 33.37** |
| PD-23 | 50 | 97.34 ± 8.36** | 435.56 ± 27.08** |
| PD-24 | 50 | 91.17 ± 9.03**$^{\#}$ | 420.33 ± 24.75**$^{\#}$ |
| PD-25 | 50 | 87.77 ± 10.58**$^{\#}$ | 412.42 ± 26.74**$^{\#}$ |
| PD-26 | 50 | 83.94 ± 7.63**$^{\#}$ | 408.97 ± 23.06**$^{\#\#}$ |
| PD-27 | 50 | 97.73 ± 8.95** | 430.05 ± 27.90** |
| PD-28 | 50 | 70.51 ± 12.45** | 352.69 ± 30.77**$^{aa}$ |

(Note: $^{Δ}$P < 0.05, $^{ΔΔ}$P < 0.01, vs. blank group; *P < 0.05, **P < 0.01, vs. moel group, $^{\#}$P < 0.05, $^{\#\#}$P < 0.01, vs. Crisaborole group; $^{a}$P < 0.05, $^{aa}$P < 0.01, ~~coupound group and~~ compound Y5 group)

Compared with Crisaborole, the compounds PD-1, PD-4, PD-6, PD-7, PD-8, PD-10, PD-12, PD-14, PD-15, PD-16, PD-17, PD-21, PD-29, PD-30 may significantly reduce the thickness of the epidermis (P≤0.01), and PD-9, PD-24, PD-25, PD-26, PD-31, PD-32, PD-33, and compound Y5 may significantly reduce the thickness of the epidermis of the dermatitis mice (P≤0.05); the compounds PD-1, PD-4, PD-6, PD-7, PD-8, PD-10, PD-12, PD-14, PD-15, PD-16, PD-17, PD-21, PD-26, PD-29, PD-30, PD-31, PD-33, and the compound Y5 may significantly reduce the thickness of the dermis of dermatitis mice (P≤0.01), and PD-3, PD-9, PD-24, PD-25, PD-32 may significantly reduce the thickness of the dermis of dermatitis mice (P≤0.05).

Compared with the compound Y5, the compounds PD-1, PD-4, PD-6, PD-7, PD-8, PD-12, PD-14, PD-15, PD-21, PD-29 may significantly reduce the thickness of the epidermis (P≤0.01), and the compound PD-16 may significantly reduce the thickness of the epidermis (P<0.05); the compounds PD-4, PD-6, PD-7, PD-12, PD-14, PD-15, PD-17, PD-29 may significantly reduce the thickness of the dermis of dermatitis mice (P≤0.01), and PD-1, PD-8, PD-16, PD-21, PD-33 may significantly reduce the thickness of the dermis of dermatitis mice (P≤0.05).

This suggests that the compound of the disclosure has a better anti-atopic dermatitis effect, and some compounds have better effects on the activity than Crisaborole and the compound Y5, thereby having good development prospects.

DESCRIPTION OF EMBODIMENTS

Embodiment 1

Preparation of PD-1

Step 1 Preparation of an Intermediate 2

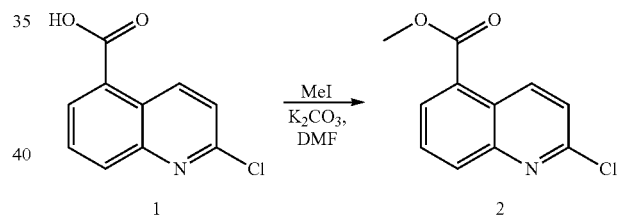

50 mL single-necked flask is charged with 1 (4.5 g, 21.7 mmol) and methyl iodide (4.58 g, 32.55 mmol), and 30 mL DMF is added to dissolve. Then, potassium carbonate (6.03 g, 43.4 mmol) is added to stir at 100° C. for 2 h until the reaction is completed through TLC detection, and then extracted with ethyl acetate, washed with saturated brine three times; the organic layer is dried, filtered, and concentrated, so as to obtain 4.2 g of a product with a yield of 87.5%.

Step 2 Preparation of an Intermediate 3

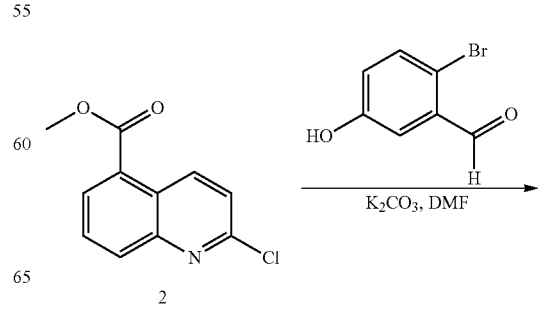

-continued

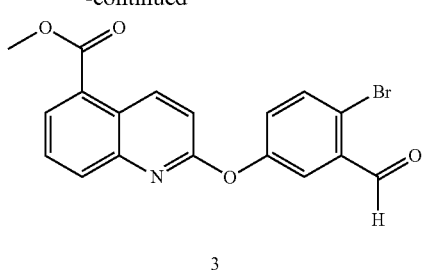

3

50 mL single-necked flask is charged with 2 (4.2 g, 20 mmol) and 2-bromo-5hydroxybenzaldehyde (4 g, 20 mmol), and 50 mL DMF is added to dissolve. Then, potassium carbonate (2.56 g, 8 mmol) is added to stir at 100° C. overnight under nitrogen until the reaction is completed through TLC detection, and then extracted with ethyl acetate, washed with saturated brine three times; the organic layer is dried, filtered, and concentrated, so as to obtain 1.5 g of a product with a yield of 20% through column chromatography.

Step 3 Preparation of an Intermediate 4

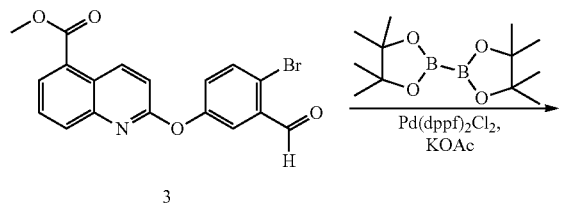

3

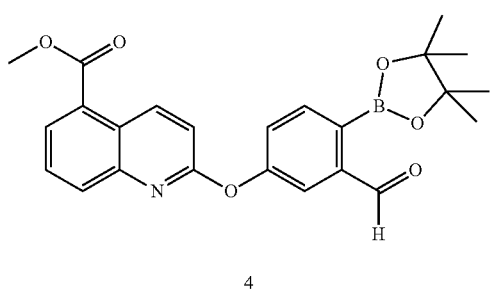

4

50 mL single-necked flask is charged with 3 (1.46 g, 3.79 mmol) and boronic acid pinacol ester (1.16 g, 4.55 mmol), and 20 mL dioxane is added to dissolve. Then, potassium acetate (1.3 g, 7.58 mmol) and palladium reagent (277 mg, 0.38 mmol) are added to stir at 100° C. for 2 hours under nitrogen until the reaction is completed through TLC detection, and then extracted with ethyl acetate, washed with saturated brine three times; the organic layer is dried, filtered, and concentrated, so as to obtain 1.6 g of a product with a yield of 97% through column chromatography.

Step 4 Preparation of PD-1

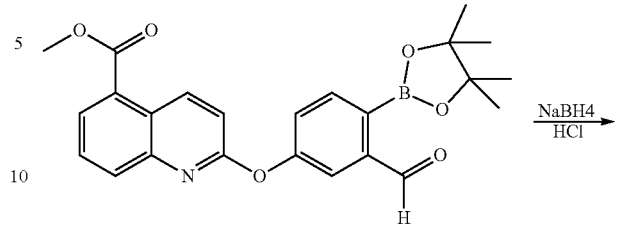

4

PD-1

50 mL single-necked flask is charged with 4 (1.6 g, 3.79 mmol), 20 ml methanol is added to dissolve, and sodium borohydride (168 mg, 4.55 mmol) is added slowly, to stir for 0.5 h at room temperature. Then, 3M hydrochloric acid is added until a white solid precipitates, and then the reaction is continued for 2 hours, followed by suction filtration, washing three times, and drying, so as to obtain the product PD1 (0.8 g, 63%). $^1$HNMR 400 MHz (DMSO-d$_6$) δ: 9.20-9.22 (m, 2H), 8.10-8.12 (m, 1H), 7.74-7.90 (m, 3H), 7.44-7.46 (s, 1H), 7.32 (d, 1H), 7.22-7.25 (m, 1H), 5.01 (s, 2H), 3.96 (s, 3H).

Embodiment 2

Synthesis of PD-2

Referring to the method of Embodiment 1, 2-chloroquinoline-5-carboxylic acid is used as a raw material to prepare the PD-2 (70 mg, yield 13%). $^1$HNMR 400 MHz (DMSO-d$_6$) δ: 13.42 (s, 1H), 9.33-9.35 (d, 1H), 9.22 (s, 1H), 8.08-8.14 (m, 1H), 7.81-7.88 (m, 2H), 7.73-7.77 (m, 1H), 7.42-7.44 (d, 1H), 7.32 (s, 1H), 7.23-7.25 (m, 1H), 5.02 (s, 2H).

Embodiment 3

Synthesis of PD-3

Referring to the method of Embodiment 1, 2-chloroquinoline-5-carboxylic acid ethyl ester is used as a raw material to prepare the PD-3 (70 mg, yield 13%), $^1$HNMR 400 MHz (DMSO-d$_6$) δ: 9.20-9.22 (m, 2H), 8.11-8.14 (d, 1H), 7.74-7.90 (m, 3H), 7.44-7.46 (d, 1H), 7.32 (s, 1H), 7.23-7.25 (m, 1H), 5.01 (s, 2H), 4.41-4.46 (m, 2H), 1.38-1.42 (m, 3H).

Embodiment 4

Synthesis of Compound PD-4

Referring to the method of Embodiment 1, 2-chloro-6-cyanoquinoline is used as a raw material to prepare the PD-4 (56 mg, 10%). $^1$HNMR 400 MHz (DMSO-d$_6$) δ: 9.24 (s, 1H), 8.86 (s, 1H), 8.53-8.55 (d, 1H), 7.94-7.97 (m, 1H), 7.82-7.84 (d, 1H), 7.75-7.77 (d, 1H), 7.46-7.48 (d, 1H), 7.34 (s, 1H), 7.24-7.26 (d, 1H), 5.03 (s, 2H).

Embodiment 5

Synthesis of PD-5

Referring to the method of Embodiment 1, 2-chloroquinoline-4-carboxylate is used as a raw material to prepare the PD-5 (34.0 mg, 62.8%). $^1$HNMR 400 MHz (DMSO-$d_6$) δ: 9.22 (s, 1H), 8.49 (d, J=8.28 Hz, 1H), 7.82 (d, J=7.78 Hz, 1H), 7.71-7.77 (m, 2H), 7.67 (s, 1 H), 7.56-7.63 (m, 1H), 7.33 (s, 1H), 7.25 (dd, J=8.03, 1.51 Hz, 1H), 5.02 (s, 2H), 4.00 (s, 3H).

Embodiment 6

Synthesis of Compound PD-6

Referring to the method of Embodiment 1, 2-chloro-6-trifluoromethylquinoline is used as a raw material to prepare the PD-6 (104 mg, 77.6%). $^1$HNMR 400 MHz (DMSO-$d_6$) δ: 9.24 (s, 1H), 8.63-8.65 (d, 1H), 8.49 (s, 1H), 7.90-7.93 (m, 1H), 7.81-7.84 (m, 1H), 7.46-7.48 (d, 1H), 7.34 (s, 1H), 7.24-7.27 (m, 1H), 5.03 (s, 2H).

Embodiment 7

Synthesis of Compound PD-7

Referring to the method of Embodiment 1, 2-chloro-5-trifluoromethylquinoline is used as a raw material to prepare the PD-7 (105.0 mg, 59.9%). $^1$HNMR 400 MHz (DMSO-$d_6$) δ: 9.23 (s, 1H), 8.54 (d, J=9.03 Hz, 1H), 7.93-8.00 (m, 2H), 7.79-7.86 (m, 2H), 7.52 (d, J=9.29 Hz, 1H), 7.35 (s, 1H), 7.26 (d, J=7.78 Hz, 1H), 5.03 (s, 2H).

Embodiment 8

Referring to the method of Embodiment 1, 2, 7-chloro-5-trifluoromethylquinoline is used as a raw material to prepare the PD-8 (33.5 mg, 39.9%). $^1$HNMR 400 MHz (DMSO-$d_6$) δ: 9.23 (s, 1H), 8.54 (d, J=9.03 Hz, 1H), 7.93-8.00 (m, 2H), 7.79-7.86 (m, 2H), 7.52 (d, J=9.29 Hz, 1H), 7.35 (s, 1H), 7.26 (d, J=7.78 Hz, 1H), 5.03 (s, 2H).

Embodiment 9

Synthesis of Compound PD-9

Referring to the method of Embodiment 1, 2-chloro-4-trifluoromethyl-6-cyano-quinoline is used as a raw material to prepare the PD-9 (87 mg, 48%). 1HNMR 400 MHz (DMSO-$d_6$) δ: 9.27 (s, 1H), 8.49 (s, 1H), 8.12-8.14 (d, 1H), 7.99 (s, 1H), 7.84-7.92 (m, 2H), 7.40 (s, 1H), 7.30-7.32 (m, 1H), 5.04 (s, 2H).

Embodiment 10

Synthesis of PD-10

Referring to the method of Embodiment 1, 2-chloroquinoline-6-carboxylic acid methyl ester is used as a raw material to prepare the PD-12 (43 mg, 41%). 1H NMR (400 MHz, DMSO) δ 9.22 (s, 1H), 8.70-8.58 (m, 2H), 8.12 (dd, J=8.8, 1.7 Hz, 1H), 7.82 (d, J=7.9 Hz, 1H), 7.71 (d, J=8.8 Hz, 1H), 7.40 (d, J=8.8 Hz, 1H), 7.33 (s, 1H), 7.24 (d, J=8.0 Hz, 1H), 5.02 (s, 2H), 3.91 (s, 3H).

Embodiment 11

Synthesis of PD-11

Referring to the method of Embodiment 1, 2-chloroquinoline-5-amide is used as a raw material to prepare the PD-13 (37 mg, 32%). 1H NMR (400 MHz, DMSO) δ 9.24 (s, 1H), 8.83 (d, J=9.1 Hz, 1H), 8.12 (s, 1H), 7.82 (d, J=8.0 Hz, 1H), 7.76-7.59 (m, 4H), 7.40-7.29 (m, 2H), 7.23 (d, J=7.9 Hz, 1H), 5.02 (s, 2H).

Embodiment 12

Synthesis of PD-12

Referring to the method of Embodiment 1, 2-chloro-5-acetylquinoline is used as a raw material to prepare the PD-12 (35 mg, 31%). 1H NMR (400 MHz, DMSO) δ 9.21 (s, 1H), 9.07 (d, J=9.2 Hz, 1H), 8.15 (dd, J=7.2, 1.2 Hz, 1H), 7.79 (dd, J=12.3, 7.8 Hz, 3H), 7.40 (d, J=9.3 Hz, 1H), 7.30 (d, J=1.4 Hz, 1H), 7.22 (dd, J=8.0, 2.0 Hz, 1H), 5.01 (s, 2H), 2.74 (s, 3H).

Embodiment 13

Synthesis of PD-13

Referring to the method of Embodiment 1, 2-chloro-6-amidoquinoline is used as a raw material to prepare the PD-13 (55 mg, 45%). $^1$H NMR (400 MHz, DMSO) δ 9.22 (s, 1H), 8.51 (d, J=8.8 Hz, 2H), 8.12 (d, J=10.3 Hz, 2H), 7.83 (d, J=7.9 Hz, 1H), 7.68 (d, J=8.8 Hz, 1H), 7.48 (s, 1H), 7.40-7.29 (m, 2H), 7.24 (d, J=9.1 Hz, 1H), 5.03 (s, 2H).

Embodiment 14

Synthesis of PD-14

Referring to the method of Embodiment 1, 2-chloro-6-acetylquinoline is used as a raw material to prepare the PD-14 (60 mg, 51%). $^1$H NMR (400 MHz, DMSO) δ 9.23 (s, 1H), 8.71 (d, J=1.9 Hz, 1H), 8.62 (d, J=8.8 Hz, 1H), 8.14 (dd, J=8.8, 2.0 Hz, 1H), 7.83 (d, J=8.0 Hz, 1H), 7.70 (d, J=8.8 Hz, 1H), 7.41 (d, J=8.8 Hz, 1H), 7.34 (d, J=1.4 Hz, 1H), 7.25 (dd, J=7.9, 2.0 Hz, 1H), 5.03 (s, 2H), 2.70 (s, 3H).

Embodiment 15

Synthesis of PD-15

According to the method of Embodiment 1, 2,7-dichloro-6-trifluoromethylquinoline is used as a raw material to prepare the PD-15 (35 mg, 33.2%). $^1$HNMR 400 MHz (DMSO-$d_6$) δ: 9.27 (s, 1H), 8.01 (d, J=8.8 Hz, 1H), 7.84 (d, J=7.9 Hz, 1H), 7.64 (d, J=8.9 Hz, 1H), 7.35 (m, 2H), 6.97 (d, J=7.9 Hz, 1H), 6.48 (d, J=8.0 Hz, 1H), 5.03 (s, 2H).

Embodiment 16

Synthesis of PD-16

According to the method of Embodiment 1, 2,7-dichloro-6-cyanoquinoline is used as a raw material to prepare the PD-16 (57 mg, 38%). $^1$H NMR (400 MHz, DMSO) δ 9.24

(s, 1H), 8.76 (s, 1H), 8.54 (d, J=8.9 Hz, 1H), 7.94 (s, 1H), 7.82 (d, J=7.9 Hz, 1H), 7.48 (d, J=8.9 Hz, 1H), 7.34 (s, 1H), 7.25 (dd, J=8.0, 2.0 Hz, 1H), 5.02 (s, 2H).

Embodiment 17

Synthesis of PD-17

According to the method of Embodiment 1, 2-chloro-4,6-trifluoromethylquinoline is used as a raw material to prepare the PD-17 (57 mg, 38%). $^1$H NMR (400 MHz, DMSO) δ 9.21 (s, 1H), 8.76-8.73 (m, 1H), 8.54 (d, J=8.9 Hz, 1H), 7.94 (s, 1H), 7.82-7.73 (m, 1H), 7.43 (d, J=8.9 Hz, 1H), 7.30 (s, 1H), 7.19 (dd, J=8.0, 2.0 Hz, 1H), 5.02 (s, 2H).

Embodiment 18

Synthesis of PD-18

According to the method of Embodiment 1, 2-chloro-4-trifluoromethylquinoline-6-carboxylic acid methyl ester is used as a raw material to prepare the PD-18 (37 mg, 38%). $^1$H NMR (400 MHz, DMSO) δ 9.11 (s, 1H), 8.46 (s, 1H), 8.10 (d, J=8.8 Hz, 1H), 7.77 (s, 1H), 7.72-7.65 (m, 2H), 7.15 (d, J=8.0 Hz, 1H), 4.89 (s, 2H), 3.79 (s, 3H).

Embodiment 19

Synthesis of PD-19

According to the method of Embodiment 1, 2-chloro-4-trifluoromethyl-6-acetylquinoline is used as a raw material to prepare the PD-19 (107 mg, 68%). $^1$H NMR (400 MHz, DMSO) δ 9.26 (s, 1H), 8.54 (s, 1H), 8.30 (d, J=8.8 Hz, 1H), 7.95-7.82 (m, 3H), 7.40 (s, 1H), 7.31 (dd, J=8.0, 1.4 Hz, 1H), 5.05 (s, 2H), 2.72 (s, 3H).

Embodiment 20

Synthesis of PD-20

According to the method of Embodiment 1, 2-chloro-4-fluoroquinoline-6-carboxylic acid methyl ester is used as a raw material to prepare the PD-20 (43 mg, 41%). $^1$HNMR 400 MHz (DMSO-d$_6$) δ: 9.30 (s, 1H), 8.06-8.08 (d, 1H), 7.81-7.84 (d, 1H), 7.62-7.64 (d, 1H), 7.28-7.34 (m, 2H), 6.97-6.99 (m, 2H), 5.04 (s, 2H), 3.45 (s, 3H).

Embodiment 21

Synthesis of PD-21

According to the method of Embodiment 1, 2-chloro-4-fluoro-6-trifluoromethylquinoline is used as a raw material to prepare the PD-21 (67 mg, 48%). $^1$HNMR 400 MHz (DMSO-d$_6$) δ: 9.26 (s, 1H), 8.03 (d, J=8.8 Hz, 1H), 7.81-7.84 (m, 2H), 7.68-7.63 (m, 1H), 7.28-7.34 (m, 2H), 6.48 (d, J=8.0 Hz, 1H), 5.03 (m, 1H).

Embodiment 22

Synthesis of PD-22

According to the method of Embodiment 1, 2-chloro-4-fluoro-6-cyanoquinoline is used as a raw material to prepare the PD-22 (51 mg, 31%). $^1$HNMR 400 MHz (DMSO-d$_6$) δ: 9.24 (s, 1H), 8.08 (d, J=8.8 Hz, 1H), 7.83 (d, J=8.8 Hz, 1H), 7.67-7.62 (m, 1H), 7.34 (d, J=8.0 Hz, 2H), 6.99 (d, J=8.0 Hz, 1H), 6.48 (d, J=8.0 Hz, 1H), 5.01 (m, 1H).

Embodiment 23

Synthesis of PD-23

According to the method of Embodiment 1, 2-chloro-6-(trifluoromethyl) naphthalene is used as a raw material to prepare the PD-23 (72 mg, 52%). $^1$HNMR 400 MHz (DMSO-d$_6$) δ: 9.24 (s, 1H), 8.08 (d, J=8.8 Hz, 1H), 7.83 (d, J=8.8 Hz, 1H), 7.67-7.53 (m, 2H), 7.34 (d, J=8.0 Hz, 2H), 6.99-6.93 (m, 2H), 6.43 (d, J=8.0 Hz, 1H), 5.02 (m, 1H).

Embodiment 24

Synthesis of PD-24

According to the method of Embodiment 1, 2-chloro-naphthalene-5-carboxylic acid methyl ester is used as a raw material to prepare the PD-24 (57 mg, 38%). $^1$H NMR (400 MHz, DMSO) δ 9.15 (s, 1H), 8.81 (d, J=9.4 Hz, 1H), 8.16-8.04 (m, 2H), 7.77 (d, J=8.6 Hz, 1H), 7.64-7.55 (m, 2H), 7.47 (dd, J=9.3, 2.7 Hz, 1H), 7.16-7.05 (m, 2H), 4.94 (s, 2H), 3.94 (s, 3H).

Embodiment 25

Synthesis of PD-25

According to the method of Embodiment 1, 2-chloro-6-cyanonaphthalene is used as a raw material to prepare the PD-25 (37 mg, 28%). $^1$H NMR (400 MHz, DMSO) δ 9.22 (s, 1H), 8.59 (s, 1H), 8.15 (d, J=9.0 Hz, 1H), 8.03 (d, J=8.6 Hz, 1H), 7.84-7.73 (m, 2H), 7.58-7.46 (m, 2H), 7.20-7.09 (m, 2H), 4.98 (s, 2H).

Embodiment 26

Synthesis of PD-26

According to the method of Embodiment 1, 2,4-dichloro-6-cyanoquinoline is used as a raw material to prepare the PD-26 (43 mg, 36%). $^1$HNMR 400 MHz (DMSO-d$_6$) δ: 9.23 (s, 1H), 8.35 (d, J=9.2 Hz, 1H), 7.81 (d, J=8.8 Hz, 1H), 7.62 (d, J=8.0 Hz, 1H), 6.92 (d, J=9.2 Hz, 1H), 6.78-6.63 (m, 2H), 6.46 (d, J=9.2 Hz, 1H), 5.04 (m, 1H).

Embodiment 27

Synthesis of PD-27

Referring to the method of Embodiment 1, 2,4-dichloro-quinoline-6-carboxylic acid methyl ester is used as a raw material to prepare the PD-27 (63 mg, 36%). $^1$H NMR (400 MHz, DMSO) δ 9.34 (s, 1H), 8.91 (d, J=1.8 Hz, 1H), 8.35 (dd, J=8.8, 2.0 Hz, 1H), 8.09 (d, J=8.8 Hz, 1H), 7.92 (d, J=8.0 Hz, 1H), 7.46 (d, J=1.6 Hz, 1H), 7.38 (dd, J=8.0, 2.1 Hz, 1H), 6.67 (s, 1H), 5.06 (s, 2H), 3.96 (s, 3H).

Embodiment 28

Synthesis of PD-28

According to the method of Embodiment 1, 2,4-dichloro-6-trifluoromethylquinoline is used as a raw material to prepare the PD-28 (23 mg, 16%). $^1$HNMR 400 MHz (DMSO-$d_6$) δ: 9.22 (s, 1H), 8.34 (d, J=9.2 Hz, 1H), 7.82 (d, J=8.8 Hz, 1H), 7.58 (d, J=8.0 Hz, 1H), 6.97 (d, J=9.2 Hz, 1H), 6.78-6.62 (m, 2H), 6.51 (d, J=9.2 Hz, 1H), 5.04 (m, 1H).

The invention claimed is:

1. A compound having a following general formula (I) or a pharmaceutically acceptable salt thereof:

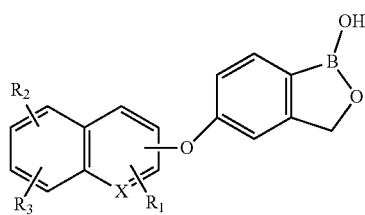

(I)

wherein $R_1$, $R_2$, $R_3$ represent an optionally substituted halogen, an alkyl of $C_1$ to $C_6$, a trifluoromethyl, a cyano, an amino, C(O)OR$_a$, COR$_a$, or OR$_a$;

$R_a$ represents H, the alkyl of $C_1$ to $C_6$, the amino or the trifluoromethyl;

X is N or CH.

2. A compound or a pharmaceutically acceptable salt thereof, the compound comprising any of the following structural formulas:

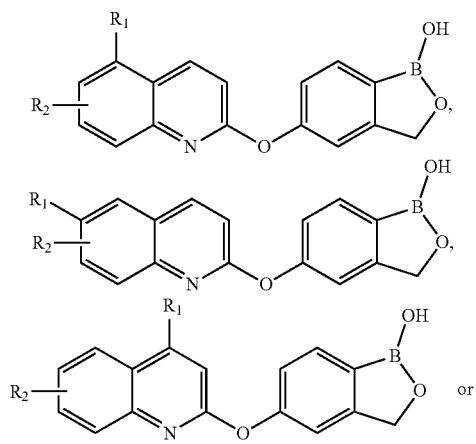

or

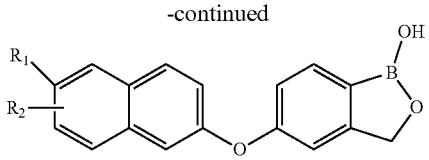

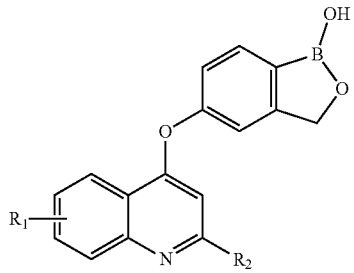

wherein $R_1$ and $R_2$ represent an optionally substituted halogen, an alkyl of $C_1$ to $C_6$, a trifluoromethyl, a cyano, an amino, C(O)OR$_a$, COR$_a$, or OR$_a$;

$R_a$ represents H, the alkyl of $C_1$ to $C_6$, the amino or the trifluoromethyl.

3. A compound or a pharmaceutically acceptable salt, the compound comprising any of the following formula:

wherein $R_1$ and $R_2$ represent an optionally substituted halogen, an alkyl of $C_1$ to $C_6$, a trifluoromethyl, a cyano, an amino, C(O)OR$_a$, COR$_a$, or OR$_a$;

$R_a$ represents H, the alkyl of $C_1$ to $C_6$, the amino or the trifluoromethyl.

4. The compound or a pharmaceutically acceptable salt thereof according to claim 1, wherein the pharmaceutically acceptable salt is a potassium salt, a sodium salt, an ammonium salt, a hydrochloride salt, a sulfate salt, a phosphate salt, a hydrobromide salt, a maleate salt, a fumarate salt, a citrate salt, a mesylate salt, a p-toluenesulfonate salt, a tartrate salt or an acetate salt of the compound having the general formula (I).

5. A pharmaceutical composition, comprising the compound or a pharmaceutically acceptable salt thereof according to claim 1, and a pharmaceutically acceptable carrier.

6. A drug for inhibiting phosphodiesterase 4, comprising the compound or a pharmaceutically acceptable salt thereof according to claim 1.

7. A drug for preventing or treating inflammation-related diseases, comprising the compound or a pharmaceutically acceptable salt thereof according to claim 1.

* * * * *